United States Patent [19]

Yang et al.

[11] Patent Number: 5,414,070

[45] Date of Patent: May 9, 1995

[54] POLY(AMIDE-ETHER-IMIDE)S

[75] Inventors: Chin-Ping Yang; Sheng-Huei Hsiao; Jiun-Hung Lin, all of Taipei, Taiwan, Prov. of China

[73] Assignee: National Science Council, Taipei, Taiwan, Prov. of China

[21] Appl. No.: 162,683

[22] Filed: Dec. 3, 1993

Related U.S. Application Data

[62] Division of Ser. No. 44,237, Apr. 7, 1993, Pat. No. 5,268,487.

[51] Int. Cl.⁶ .............................. C08G 73/10
[52] U.S. Cl. ....................... 528/310; 528/26; 528/170; 528/171; 528/172; 528/173; 528/174; 528/289; 528/335; 528/340; 528/350; 528/353
[58] Field of Search ............... 528/289, 310, 335, 340, 528/350, 353, 170, 171, 172, 173, 174, 26; 548/462, 456

[56] References Cited

U.S. PATENT DOCUMENTS

| | | | |
|---|---|---|---|
| 3,461,136 | 8/1969 | Pruckmayr et al. | 548/456 |
| 4,118,392 | 3/1979 | Schmidt et al. | 528/289 |
| 4,145,351 | 10/1979 | Salle et al. | 528/289 |

*Primary Examiner*—Samuel A. Acquah
*Assistant Examiner*—P. Hampton-Hightower
*Attorney, Agent, or Firm*—W. Wayne Liauh

[57] ABSTRACT

Disclosed is a poly(amide-ether-imide) and the preparation of the same. An ether chain-containing aromatic diamine is subject to thermal condensation with trimellitic anhydride (TMA) in a polar solvent to obtain diimide dicarboxylic acid, followed by polycondensing the diimide dicarboxlic acid with diamine to form the poly(amide-ether-imide). The poly(amide-ether-imide) of the present invention has superior strength, heat resistance, and processability. The preparation of the present invention is simple and economic.

16 Claims, No Drawings

POLY(AMIDE-ETHER-IMIDE)S

This application is a divisional application of application Ser. No. 08/044,237, filed on Apr. 7, 1993, now U.S. Pat. No. 5,268,487.

BACKGROUND OF THE INVENTION

The present invention relates to a poly(amide-ether-imide) and the preparation of the same, and in particular relates to a poly(amide-ether-imide) prepared by subjecting a cyclized imide-containing dicarboxylic acid to polycondensation with an aromatic diamine.

Poly(amide-imide)s are characterised as high performance polymeric materials having both superior heat resistance of polyimide and superior toughness, and processability of polyamide. The most economic and simple method for the preparation Of poly(amide-imide) is by the use of trimellitic anhydride (TMA). TMA has the characteristics of both anhydride and carboxylic acid, hence when it is subjected to polycondensation with diamines, poly(amide-imide)s are formed. However, difficulties are encountered when it is desired to prepare linear poly(amideimide)s with high molecular weight from TMA and diamine. In general, poly(amide-imide)s are prepared by first activating TMA to 4-chloroformyl phthalic anhydride, then subjecting the anhydride to low temperature solution polycondensation with diamine to form poly(amide-amic acid), and followed by cyclizing the amic acid by the film-baking method or high temperature ring-closing method, or the addition of condensing agents, such as acetic acid anhydride. However, there are several problems with the above-mentioned method, which are described as follows.

(1) Activation of TMA increases the manufacturing cost and the operation procedures. The activated TMA is unstable and is easily hydrated and degraded.

(2) As the polyamide-amic acid prepared by low temperature polycondensation contains strong acid (HCl), the amide bonds of the amic acid will break when subsequently subjected to cyclization by direct baking or by the addition of solvents at an elevated temperature. This breakage of amide bonds will cause the reduction of the molecular weight of the resultant products.

(3) The manufacturing cost will also increase if a treatment with acetic acid anhydride is used.

To overcome the above problems, U.S. Pat. Nos. 3,920,612 and 4,048,144 disclose a process comprising first subjecting TMA to polycondensation with amine to form diacid of imide, then activatiing the diacid to acid chloride, and followed by polycondensing the acid chloride at low temperature. However, high manufacturing cost is still a problem and the intermediate acid chloride is not easily purified.

Japan laid-open Patents Nos. Sho 44-19274, Sho 46-20068 and Sho 50-33120 describe a process for preparing a poly(amide-imide). The process includes reacting diisocyanates with TMA or its derivates in specific solvents and catalysts at an elevated temperature. As the source of diisocyanates is limited and the diisocyanates are not as stable as diamine in storage, this process is not satisfactory.

Japan laid-open Patent Nos. Sho 49-4077, Sho 58-180532 and British Patent No. 1383480 describe a poly(amide-imide) prepared by direct copolymerizing TMA and diamine in the presence of catalysts at a temperature of 200° C. However, at such a temperaure, the polymer is easily coloured and a linear polymer is not necessarily formed.

Accordingly, a novel synthetic method of poly(amideimide) was developed by the inventors in 1989, which method comprises first preparing an imide-containing dicarboxylic acid by thermocondensation, and then subjecting the acid to polycondensation with diamine directly by using a phosphite condensing agent. The manufacturing cost of this method is low and high molecular weight polymers are obtainable.

SUMMARY OF THE INVENTION

It is therefore an object of the present invention to provide a poly(amide-ether-imide) with superior heat resistance, strength, and processibility.

Another object of the present invention is to provide a economic and simple method for the preparation of poly(amide-ether-imide).

DETAILED DESCRIPTION OF THE INVENTION

In order to attain the above objects, the present invention uses ether chain-containing aromatic diamines as raw material in the preparation of poly(amide-ether-imide)s. Specifically, the process of the present invention comprises subjecting an ether chain-containing aromatic diamine to thermocondensation with TMA in a polar solvent to form diimide dicarboxylic acid, followed by polycondensing the diimide dicarboxylic acid with diamine.

Suitable ether chain-containing aromatic diamines used in the present invention are derivative of bisphenol, which has the following formula:

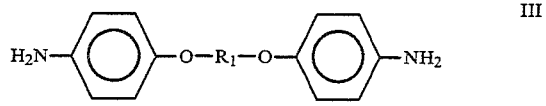

wherein $R_1$ represents

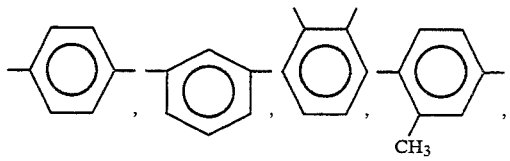

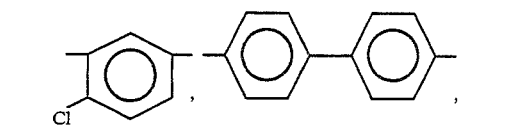

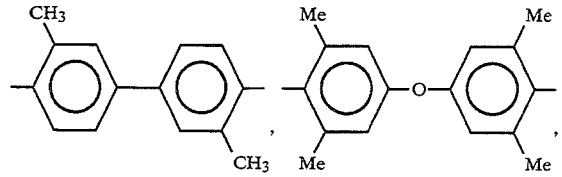

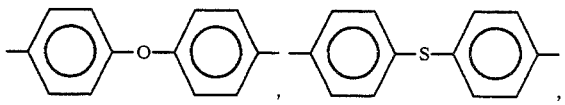

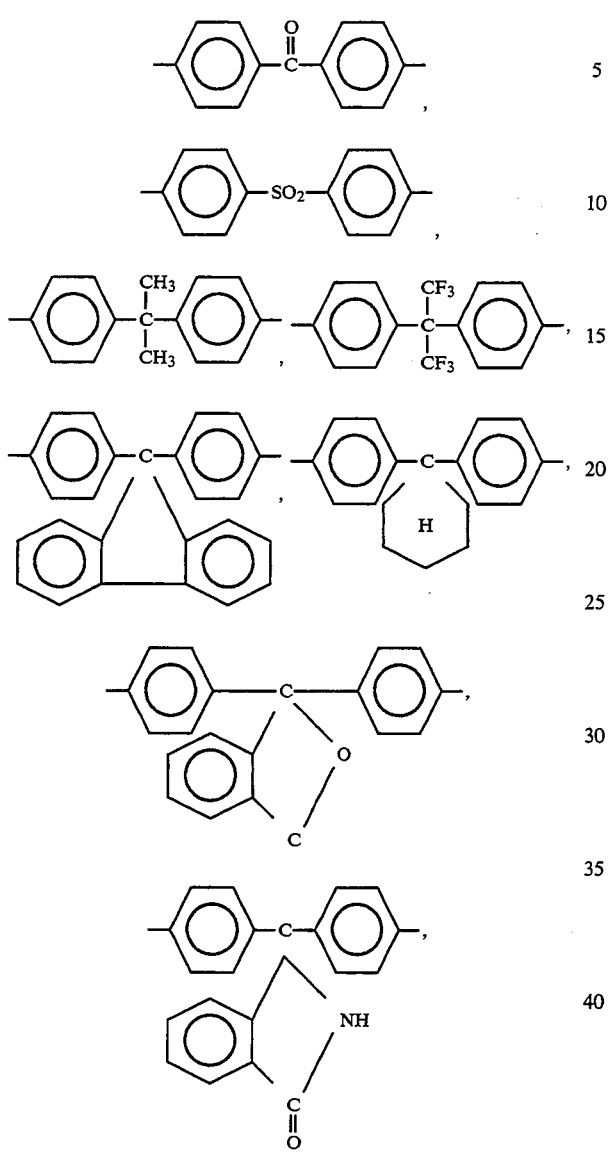

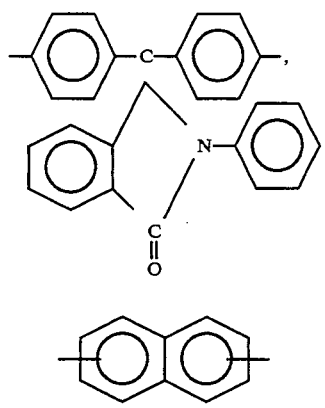

These ether chain-containing aromatic diamines are prepared by thermocondensing various bisphenols with 4-chloronitrobenzenes or thermocondensing dihalides with 4-aminophenols in a polar solvent of inorganic base, followed by a hydrogenated reduction. The bisphenol used, for example, can be any one of the following: hydroquinone, resorcinol, catechol, methylhydroquinone, 4-chlororesorcinol, 4,4'-biphenol, 3,3'-dimethyl-4,4'biphenol, 3,3', 5,5'-tetramethyl-4,4'-biphenol, 4,4'-dihydroxyphenyl ether, 4,4'-dihydroxyphenyl sulfide, 4,4'-dihydroxybenzophenone, 4,4'-dihydroxyphenyl sulfone, 2,2bis(4-hydroxyphenyl)propane, 2,2-bis(4-hydroxyphenyl)hexafluoropropane, 1,1-bis(4-hydroxyphenyl)-1-phenyl ethane, 9,9-bis(4-hydroxyphenyl)fluorene, 1,1-bis(4-hydroxyphenyl)cyclohexane, phenolphthalein, 3,3-bis(4-hydroxyphenyl)phthalimidine, N-phenyl-3,3-bis(4-hydroxyphenyl)phthalimidine, and dihydroxynaphthalenes (2,3- , 2,6- , 2,7-1,5- , 1,6- , 1,7- ).

The synthesis of diimide dicarboxylic acid (II) comprises heating and dehydrating ether chain-containing aromatic diamines and TMA at a molar ratio of 1:2 in an appropriate solvent to polycondense. Suitable solvents includes DMF, DMAc, NMP, DMSO, and sulfolane. The reaction scheme of this synthesis is illustrated as below:

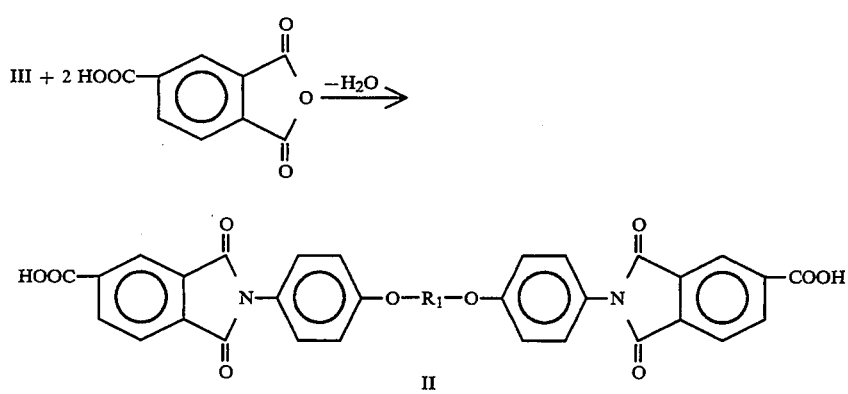

In the polycondensation of the poly(amide-ehterimide) of the present invention from diimide dicarboxylic acid(II) and aromatic diamine, triphenyl phosphite/pyridine are used as condensing agents. Suitable aromatic diamines have the formula of $H_2N-R_2-NH_2$, wherein $R_2$ represents

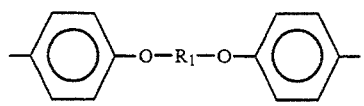

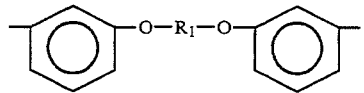

(Wherein $R_1$ represents the bisphenol components as formula III)

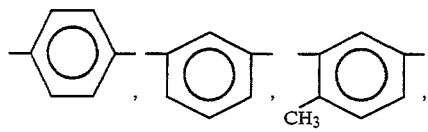

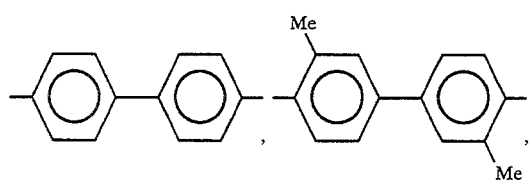

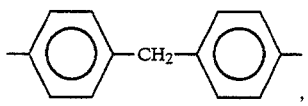

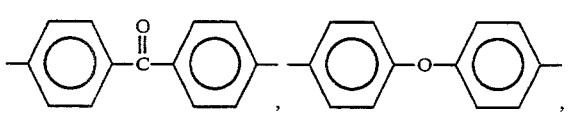

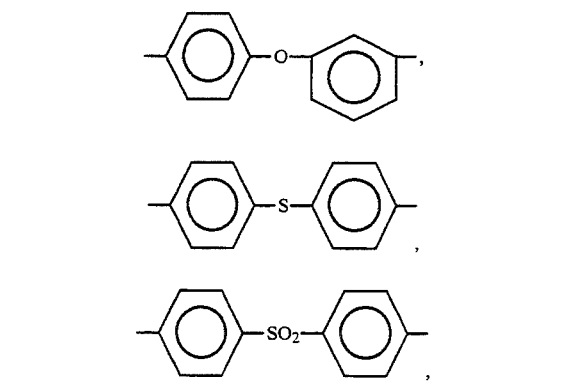

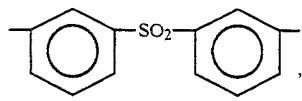

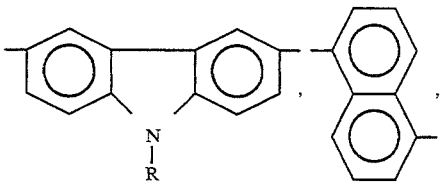

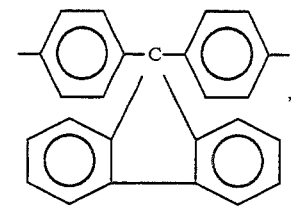

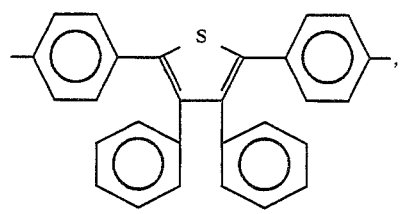

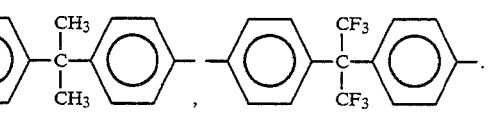

In other words, the diamines include the following: p-phenylenediamine, m-phenylenediamine, 2,4-toluenediamine, 4,4'-biphenylenediamine, 3,3'-dimethyl-4,4'-diaminobiphenyl, 4,4'-methylene dianiline, 4,4'-diaminobenzophenone, 4,4'-oxydianiline, 3,4'-oxydianiline, 4,4'-diaminodiphenyl sulfide, 4,4'-diaminodiphenyl sulfone, 3,3'-diaminodiphenyl sulfone, N-methylcarbozole-3,6-diamine, 1,5-naphthalene diamine, 9,9-bis(4-aminophenyl)fluorene, 2,5-bis(4-aminophenyl)-3,4-diphenylthiophene, 1,4-bis(4-aminophenoxy)benzene, 1,3-bis(4-aminophenoxy)benzene, 1,2-bis(4-aminophenoxy)benzene, bis[4-(4-aminophenoxy)phenyl]ether, 4,4-bis(4-aminophenoxy)biphenylene, 2,4-bis[4-(4-aminophenoxy)phenyl]propane, 2,2-bis[4-(4-aminophenoxy)phenyl]hexafluoropropane, and 2,2-bis[4-(4-aminophenoxy)phenyl]sulfone.

The reaction scheme of this synthesis is illustrated as below:

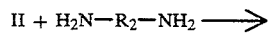

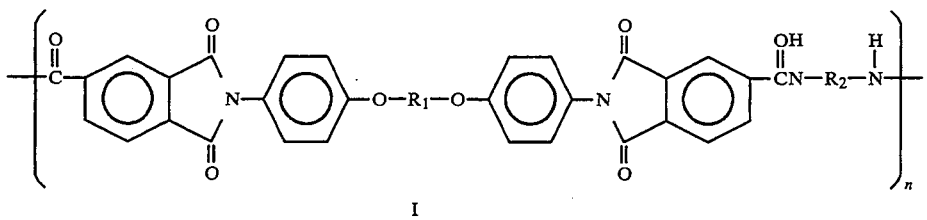

I

This invention is more specifically described by the following illustrative examples.

Preparative Example 1

To a 100 ml flask containing 1,4-bis(4-aminophenoxy)benzene (4.38 g) and TMA (5.76 g), anhydrous, purified DMF(30 ml) was added, stirred and allowed to react until a clear solution resulted. To this solution was added 10 ml of toluene. A Dean-Stark was connected to the flask, and heated in oil bath at 140° C. to remove the resulted water (about 0.55 ml) by azeotropic distillation. After the reaction was completed, the toluene was removed by distillation. After cooling, the precipitated yellow solids were isolated by filtration and washed throughly with methanol. The yield was 9.4 g (98%), m.p. 399° C.(DSC).

Elemental analysis data: calc. C: 67.50%, H: 3.15%, N: 4.37% found C: 67.40%, H: 3.19%, N: 4.32%

The product, 1,4-bis(4-trimellitimidophenoxy)benzene, has the following molecular structure:

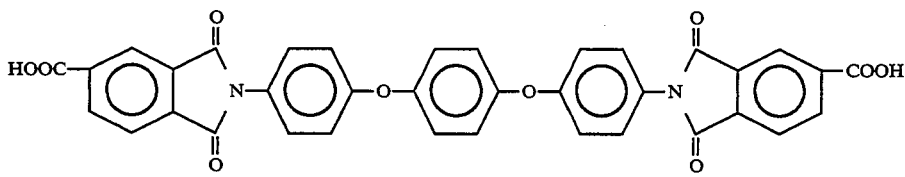

The following ether chain-containing diimide dicarboxylic acids were prepared in a similar way. The yields were all above 90%.

| | m.p.(°C.) |
|---|---|
| 1,3-bis (4-trimellitimidophenoxy)benzene | 350 |
| 2,5-bis (4-trimellitimidophenoxy)toluene | 357 |
| 4,4-bis (4-trimellitimidophenoxy)biphenylene | 414 |
| bis [4- (4-trimellitimidophenoxy)phenyl]ether | 351 |
| bis [4- (4-trimellitimidophenoxy)phenyl]sulfide | 388 |
| 4,4-bis (4-trimellitimidophenoxy)benzophenone | 376 |
| bis [4- (4-trimellitimidophenoxy)phenyl]sulfone | 323 |
| 2,2-bis [4-(4-trimellitimidophenoxy)phenyl]propane | 329 |
| 2,2-bis [4-(4-trimellitimidophenoxy)phenyl]hexafluoropropane | 338 |
| 1,1-bis [4-(4-trimellitimidophenoxy)phenyl]-1-phenylethane | 299 |
| 9,9-bis [4-(4-trimellitimidophenoxy)phenyl]fluorene | 374 |
| 1,1-bis [4-(4-trimellitimidophenoxy)phenyl]cyclohexane | 309 |
| 3,3-bis [4-(4-trimellitimidophenoxy)phenyl]phthalide | 279 |
| 3,3-bis [4-(4-trimellitimidophenoxy)phenyl]phthalimidine | 210 |
| N-phenyl,3,3-bis [4-(4-trimellitimidophenoxy)phenyl]phthalimidine | 334 |

Preparative Example 2

To a 100 ml flask containing 1,7-bis(4-aminophenoxy)naphthalene (3.4 g) and TMA (4.1 g), anhydrous, purified DMF(15 ml) was added, stirred and allowed to react until a clear solution resulted. To this solution was added 10 ml toluene. A Dean-Stark was connected to the flask, and heated in oil bath at 140° C. to remove the resultant water (about 0.36 ml) by azeotropic distillation. After the reaction was completed, the toluene was removed by distillation. After cooling, the precipitated yellow solids were isolated by filtration and washed throughly with methanol. The yield was 6.48 g (94%), m.p.>400° C.(DSC).

Elemental analysis data: calc. C: 69.56%, H: 3.21%, N: 4.06% found C: 69.39%, H: 3.38%, N: 4.05%

The product, 1,7-bis(4-trimellitimidophenoxy)naphthlene has the following molecular structure:

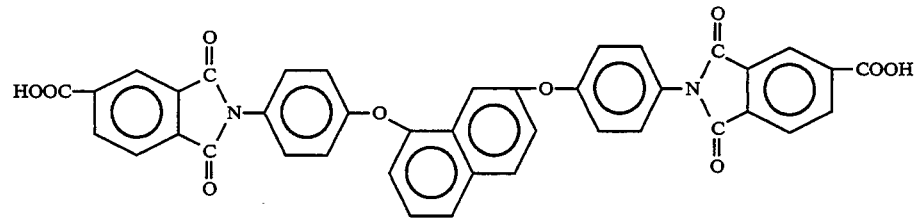

The following ether chain-containing diimide dicarboxylic acids were prepared in a similar way:

| | m.p.(°C.) | yield |
|---|---|---|
| 2,3-bis(4-trimellitimidophenoxy)naphthalene | 340 | 85% |
| 2,6-bis(4-trimellitimidophenoxy)naphthalene | 402 | 98% |
| 2,7-bis(4-trimellitimidophenoxy)naphthalene | 366 | 97% |
| 1,5-bis(4-trimellitimidophenoxy)naphthalene | 436 | 99% |
| 1,6-bis(4-trimellitimidophenoxy)naphthalene | >440 | 95% |

Preparative Example 3

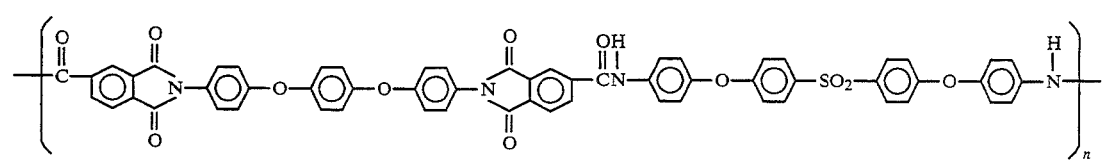

To a 300 ml flask containing 1,2-bis(4-aminophenoxy)benzene (8.76 g) and TMA (11.7 g), anhydrouse DMF(40 ml) was added, and stirred at 40° C. until dissolution. To this solution was added 20 ml anhydrous toluene, boiled and stirred by azeotropic distillation for 15 hours to remove water. The toluene was removed by distillation, cooled to room temperature, and a suitable amount of methanol was added until the precipitation of yellow solids. The precipitated yellow solids were placed overnight, filtered, washed throughly with methanol, and dried. The product was a yellow powder of 18.86 g yield (99%), m.p. 320° C.(DSC).

Elemental analysis data: calc. C: 67.48%, H: 3.25%, N: 4.37% found C: 67.68%, H: 3.24%, N: 4.43%

The product, 1,2-bis(4-trimellitimidophenoxy)benzene has the following molecular structure:

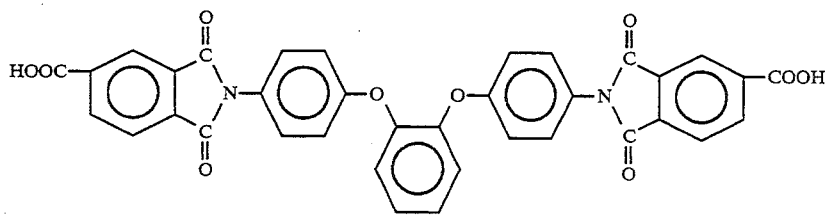

Example 1

In a 50 ml flask, was placed 4,4′-bis (4-trimellitimidophenoxy)benzene (0.801 g; 1.25 mmol), 2,2-bis [4-(4-aminophenoxy)phenyl]sulfone (0.540 g; 1.25 mmol), N-methyl-2-pyrrolidone (NMP, 8 ml), calcium chloride (0.8 g), pyridine (1.6 ml), and a condensing agent, triphenyl phosphite (0.8 ml), which were stirred and allowed to react in a 100° C. oil bath for 3 hours. A viscous solution resulted. The viscous solution was then poured into a stirred methanol. The product was a silk-like polymer of 1.319 g yield (100%), with an inherent viscosity of $\eta_{inh}$ of 1.10 dl/g (0.5 g/dl DMAc, 30° C.). Other properties of the product were measured and described as below.

Elemental analysis data: $(C_{60}H_{36}N_4O_{12}S.H_2O)_n$ calc. C: 68.30%, H: 3.63%, N: 5.31% found C: 68.19%, H: 3.96%, N: 4.98%

Mechanical strength:
tensile strength at break=62 MPa
elongation at break=9%
initial modulus=1.5 GPa
10% thermal weight loss temperature:
525° C. in air, 521° C. in N₂
Molecular structure:

Example 2

To a 50 ml flask, 2, 5-bis(4-trimellitimidophenoxy)toluene (0.818 g; 1.25 mmol), 2,2-bis[4-(4-aminophenoxy)phenyl]ether (0.481 g; 1.25 mmol), NMP (8 ml), calcium chloride (0.7 g), pyridine (1.5 ml), and a condensing agent of triphenyl phosphite (0.8 ml) were added, which were stirred in a 100° C. oil bath for three hours, the other procedures were repeated as in Example 1. A quantitative yield amount of poly(amide-imide) was obtained, which has an inherent viscosity $\eta_{inh}$ of 1.26 dl/g in DMAc. Other properties of the product are described as follows:

Elemental analysis data: $(C_{61}H_{38}N_4O_{11}.H_2O)_n$ calc. C: 71.75%, H: 3.95%, N: 5.48% found C: 71.09%, H: 4.16%, N: 5.46%

Mechanical strength:
tensile strength at break=76 MPa
elongation at break=10%
initial modulus=1.70 GPa
10% thermal weight loss temperature:
512° C. in air, 519° C. in N₂
Molecular structure:

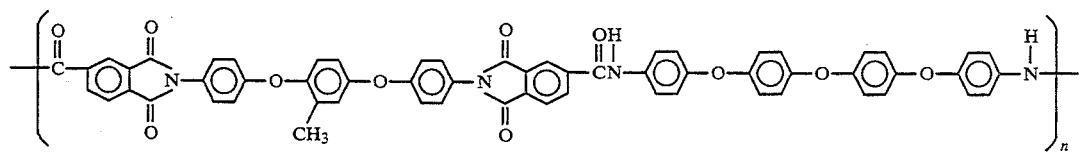

Example 3

The same procedures as in Example 2 were repeatd, except that 2,2-bis [4-(4-aminophenoxy)phenyl]ether was replaced with m-phenylene diamine. The inherent viscosity $\eta_{inh}$ thereof was measured as 1.58 dl/g in DMAc. Other properties of the product are described as follows:

Mechanical strength:
strength at yield point=85 MPa
tensile strength at break=78 MPa
elongation at break=19%
initial modulus=1.69 GPa
10% thermal weight loss temperature:
477° C. in air, 520° C. in N₂
Molecular structure:

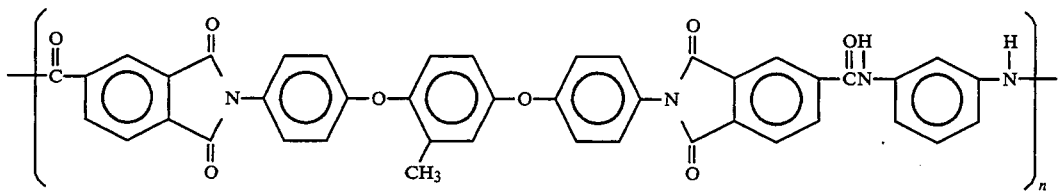

Example 4

To a 50 ml flask, bis[4- (4-trimellitimidophenoxy)-phenyl]ether (0.916 g; 1.25 mmol), 2,5-bis[4-(4-amino-phenyl)-3,4-diphenyl]thiophene (0.523 g; 1.25 mmol), NMP(8 ml), calcium chloride (0.76 g), pyridine (1.6 ml), and condensing agent of triphenyl phosphite (0.8 ml) were added, and stirred in a 100° C. oil bath for 3 hours, according to the same procedures as in Example 1. The resultant product had an inherent viscosity $\eta_{inh}$ of 1.46 dl/g in DMAc. Other properties of the product are described as follows:

Mechanical strength:
tensile strength at break=97 MPa
elongation at break=39%
initial modulus=2.36 GPa
10% thermal weight loss temperature:
489° C. in air, 565° C. in $N_2$
Molecular structure:

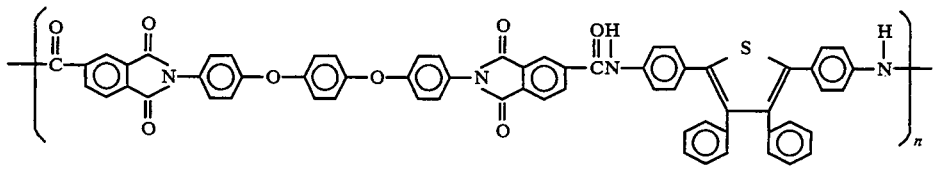

Example 5

To a 50 ml flask, 1.25 mmol of bis[4-(4-trimellitimido-phenoxy)phenyl]sulfone, 1.25 mmol of 4,4'-oxydianiline, anhydrous calcium chloride (0.76 g), NMP (8 ml), pyridine (1.6 ml), and condensing agent of triphenyl phosphite (0.8 ml) were added, stirred and allowed to react in a 100° C. oil bath for 3 hours, according to the same procedures as described in Example 1. The resultant poly(amide-imide) had a $\eta_{inh}$ of 0.81 dl/g(DMAc). Other properties are described as follows:

Mechanical strength:
strength at yield point=81 MPa
tensile strength at break=79 MPa
elongation at break=19%
initial modulus=2.14 GPa
Molecular structure:

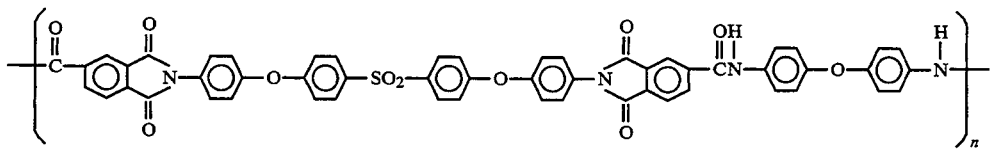

Example 6

To a reaction flask, 0.948g (1.25 mmol) of 2,2-bis[4-(4-trimellitimidophenoxy)phenyl]propane, 0.513 g (1.25 mmol) of 2,2-bis[4-(4-aminophenoxy)phenyl]propane, anhydrous calcium chloride (0.8 g), NMP (8 ml), pyridine (1.5 ml), and triphenyl phosphite (0.8 ml) were added, stirred, and allowed to react at 100° C. for 3 hours, according to the same procedures as described in Example 1. A quantitative yield of polymer was produced, which had a $\eta_{inh}$ of 1.24 dl/g(DMAc). Other properties are described as follows.

Elemental analysis data: $(C_{72}H_{52}N_4O_{10} \cdot 1.5H_2O)_n$ calc. C:74.53%, H:4.78%, N:4.83% found C:74.78%, H:4.36%, N:4.88%

Mechanical strength:
strength at yield point=85 MPa
tensile strength at break=88 MPa
elongation at break=53%
initial modulus=2.34 GPa
10% thermal weight loss temperature:
478° C. in air, 519° C. in $N_2$
Molecular structure:

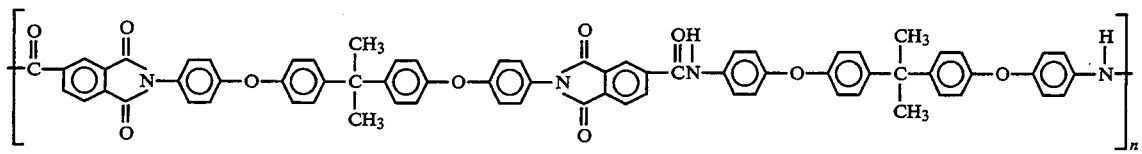

Example 7

To a reaction flask 1.083 g (1.25 mmol) of 2,2-bis[4(4-trimellitimidophenoxy)phenyl]hexafluoropropane, 0.720 g (1.25 mmol) of N-phenyl-3,3-bis[4-(4-aminophenoxy)phenyl]phthalimidine, calcium chloride (0.8 g), NMP (8 ml), pyridine (1.6 ml), and triphenyl phosphite (0.8 ml) were added, stirred, and allowed to react at 100° C. for 3 hours, according to the same procedures as described in Example 1. A polymer was produced, which had a $\eta_{inh}$ of 0.72 dl/g(DMAc). Other properties are described as follows:

Mechanical strength:
strength at yield point=82 MPa
tensile strength at break=77 MPa
elongation at break=13%
initial modulus=2.28 GPa
10% thermal weight loss temperature:
501° C. in air, 540° C. in $N_2$
Molecular structure:

Example 9

To a 50 ml flask 2.5 mmol of N-phenyl-3,3-bis[4-(4-trimellitimidophenoxy)phenyl]phthalimidine, 2.5 mmol of 4,4'-oxydianiline, anhydrous calcium chloride (0.6 g), NMP (6 ml, and extra 5.5 ml was added thereafter, because the difficulties of stirring due to high viscosity), pyridine (1.4 ml), and condensing agent of triphenyl phosphite (0.8 ml) were added, stirred and allowed to react for 3 hours, according to the same procedures as described in Example 1. A polymer was produced with a $\eta_{inh}$ of 0.87 dl/g(DMAc). Other properties are described as follows:

Mechanical strength:
tensile strength at break=89 MPa

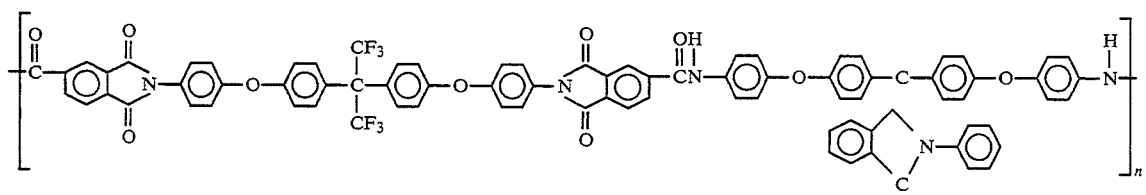

Example 8

To a 50ml reaction flask 1.026 g (1.25 mmol) of 1,1-bis[4-(4-trimellitimidophenoxy)phenyl]-1-phenylethane, 0.365 g (1.25 mmol) of 1,3-bis(4-aminophenoxy)benzene, calcium chloride (0.6 g), NMP (6 ml), pyridine (1.2 ml), and triphenyl phosphite (0.8 ml) were added, stirred and allowed to react at 100° C. for 3 hours, according to the same procedures as described in Example 1. A polymer was produced, which had a $\eta_{inh}$ of 1.07 dl/g(DMAc). Other properties are described as follows:

Elemental analysis data: $(C_{68}H_{44}N_4O_{10}\cdot 2H_2O)_n$ calc. C:73.40%, H:4.56%, N:5.04% found C:73.50%, H:4.34%, N:4.98%

Mechanical strength:
strength at yield point=79 Mpa
tensile strength at break=83 Mpa
elongation at break=9%
initial modulus=1.78 Gpa
10% thermal weight loss temperature:
508° C. in air, 528° C. in $N_2$
Molecular structure:

elongation at break=9%
initial modulus=2.38 GPa
Molecular structure:

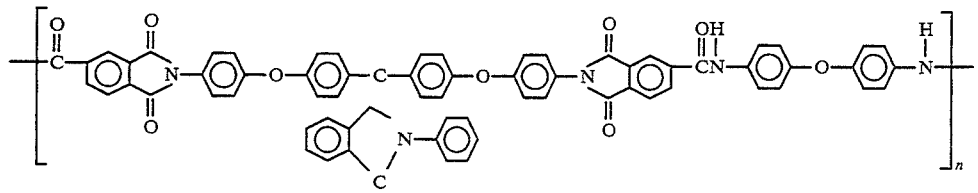

Example 10

To a 50 ml reaction flask, 2,7-bis(4-trimellitimidophenoxy)naphthalene (0.86 g; 1.25 mmol), m-phenylenediamine (0.135 g; 1.25 mmol), NMP (8 ml), calcium chloride (0.8 g), pyridine (1.6 ml), and a condensing agent of triphenyl phosphite (0.8 ml) were added, and allowed to react in a 100° C. for 3 hours. The resultant viscous solution was then poured into a stirred methanol to provide a stringy polymer precipitate. After washing with methanol and hot water throughly, the polymer was dried to yield 0.953 g product(100%). The product had an inherent viscosity of $\eta_{inh}$ of 1.57 dl/g (0.5 g/dl DMAc, 30° C.). Other properties are described as follows:

Elemental analysis data: $(C_{67}H_{44}N_4O_{10}\cdot H_2O)_n$ calc C: 69 10% H: 3 75%, N: 7 01% found C: 69 39% H: 3 69%, N: 7 03%

Mechanical strength:
tensile strength at break=74 MPa
elongation at break=9%

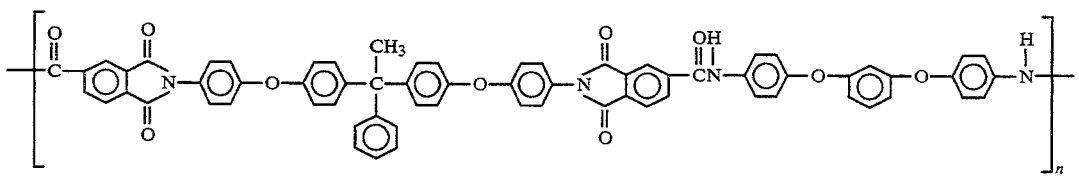

initial modulus=1.5 GPa
10% thermal weight loss temperature:
506° C. in air, 565° C. in N₂
Molecular structure:

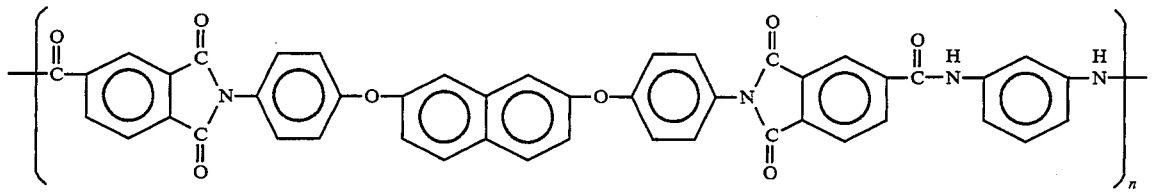

Example 11

To a 100 ml reaction flask, 0.8 g (1.25 mmol) of 1,2bis(4-trimellitimidophenoxy)benzene, 0.25 g (1.25 mmol) of 4,4'-oxydianiline, anhydrous calcium chloride (0.7 g), NMP (8 ml), pyridine (1.4 ml), and triphenyl phosphite (0.8 ml) were added, stirred and allowed to react in a 100° C. oil bath under a nitrogen atmosphere for 3 hours. The resultant viscous solution was slowly poured to a stirred methanol to yield a stringy polymer precipitate. After being soaked in methanol and warm water for 4 hours respectively, the resultant polymers was dried to yield 1.00 g polymer(100%). The pollymer had an inherent viscosity of 1.34 dl/g(DMAc-1% LiCl). A tough film of the product could be cast from NMP. Other properties are described as follows:
Mechanical strength:
strength at yield point=97 MPa
tensile strength at break=89 MPa
elongation at break=11%
initial modulus=2.37 GPa
Molecular structure:

Example 12

The same procedures as described in Example 11 were repeated, except that 4,4'-oxydianiline was replaced with 4,4'-diaminodiphenyl sulfide. The resultant product had an inherent viscosity of 1.2 dl/g. The mechanical properties of the film cast from DMAc were:
strength at yield point=76 MPa
tensile strength at break=67 MPa
elongation at break=11%
initial modulus=2.63 GPa.
Molecular structure:

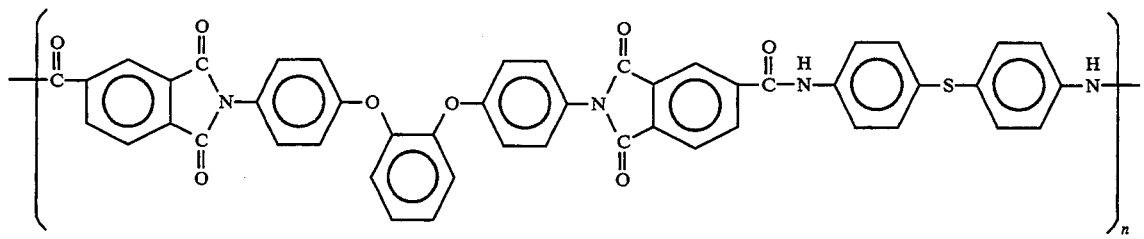

Example 13

A diimide dicarboxylic acid was prepared by condensing 2,2-bis[4-(4-aminophenoxyl)phenyl]propone (1.0 mol) and TMA (2.0 mol) in DMF according to the procedures as described in preparative Example 1. 1.25 mmole of the resultant diimide dicarboxylic acid and 1,2-bis(4-aminophenoxy)benzene (1.25 mmol) were added to a 100 ml reaction flask. Solvents and a condensing agent, including anhydrous calcium (0.7 g), NMP (8 ml), pyridine (1.2 ml), and triphenyl phosphite (0.8 ml) were then added, stirred and allowed to react in a 100° C. glycerol bath for 3 hours(an extra 3 ml of NMP was added when the viscosity increased after 1 hour of reaction). After the completion of the reaction, the resultant viscous solution was poured to a stirred methanol solution to yield a stringy polymer precipitate (100%). The solid had an inherent viscosity of 1.9 dl/g (DMAc-5%LiCl, 30° C.). The mechannical porperties of the film cast from DMAc were:
Mechanical strength:
strength at yield point=83 MPa
tensile strength at break=72 MPa
elongation at break=17%
initial modulus=2.28 GPa
Molecular structure:

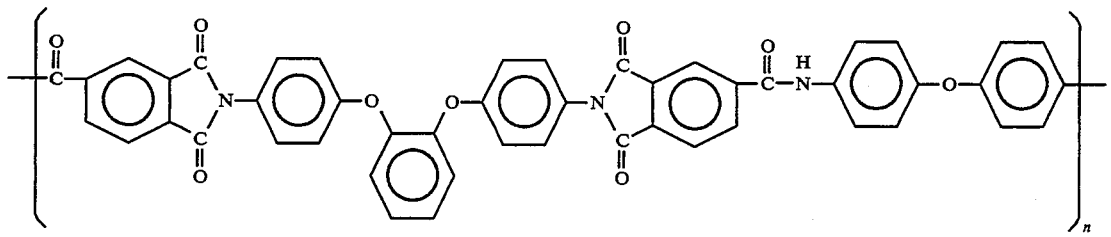

What is claimed is:

1. A poly(amide-ether-imide of the formula:

$$\left[ -C(=O)-\text{[phthalimide]}-N-\text{[phenyl]}-O-R_1- -O-\text{[phenyl]}-N-\text{[phthalimide]}-C(=O)(OH)-N(H)-R_1-N(H)- \right]_n \quad I$$

wherein R₁ is selected from the group consisting of:

[biphenyl], [dimethyl-biphenyl with CH₃ groups],

[chloro-terphenyl with Cl],

[methyl-biphenyl with CH₃ groups], [tetramethyl-biphenyl with Me groups],

[diphenyl ether], [diphenyl sulfide],

[benzophenone],

[diphenyl sulfone],

-continued

[isopropylidene diphenyl with CH₃, CH₃],

[hexafluoroisopropylidene diphenyl with CF₃, CF₂],

[triphenylmethane group],

[fluorene-type bis-diphenyl], [cycloheptyl-bridged bis-diphenyl with H],

[phthalide-type structure with O, C=O],

[phthalimidine-type structure with NH, C=O],

[N-phenyl phthalimidine structure with N, C=O]

-continued
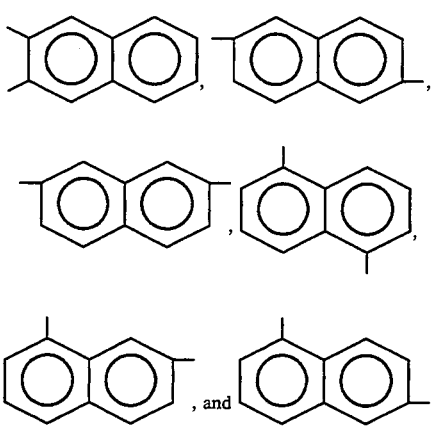
and $R_2$ is selected from the group consisting of:
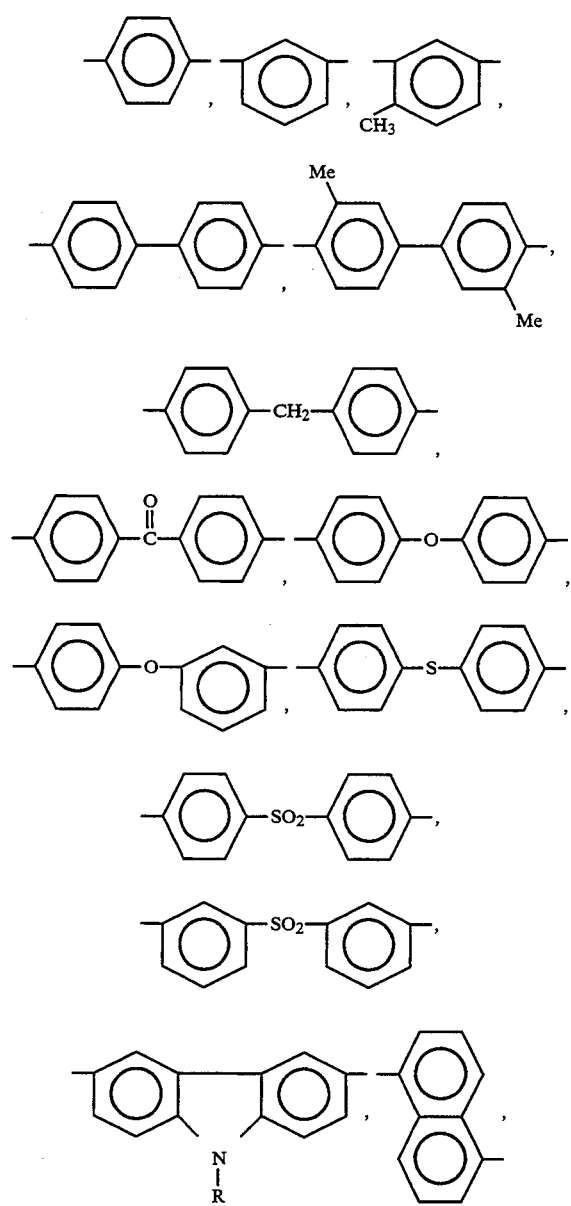
-continued
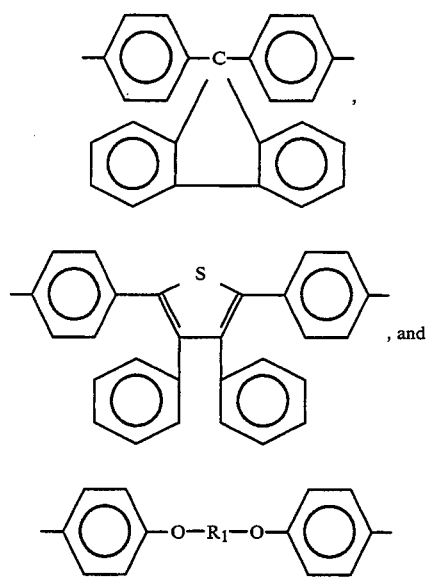
wherein R is an hydrogen atom or $CH_3$— and $R_1$ is defined above.
2. A poly(amide-ether-imide) as claimed in claim 1, wherein $R_1$ is
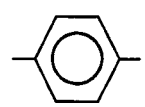
and $R_2$ is
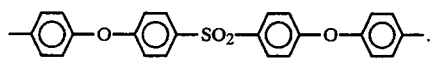
3. A poly(amide-ether-imide) as claimed in claim 1, wherein $R_1$ is
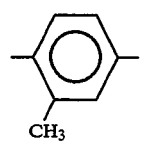
and $R_2$ is
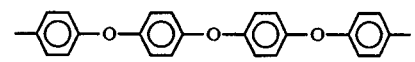
4. A poly(amide-ether-imide) as claimed in claim 1, wherein $R_1$ is
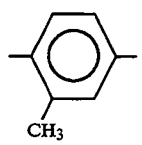
and $R_2$ is

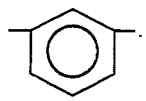

5. A poly(amide-ether-imide) as claimed in claim 1, wherein $R_1$ is

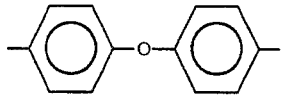

and $R_2$ is

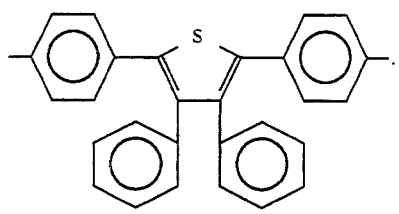

6. A poly(amide-ether-imide) as claimed in claim 1, wherein $R_1$ is

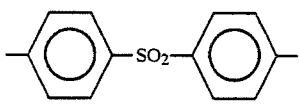

and $R_2$ is

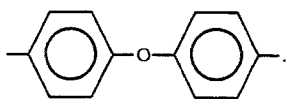

7. A Poly(amide-ether-imide) as claimed in claim 1, wherein $R_1$ is

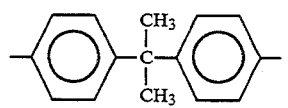

and $R_2$ is

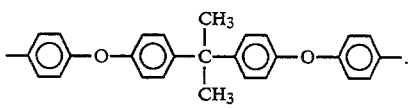

8. A Poly(amide-ether-imide) as claimed in claim 1, wherein $R_1$ is

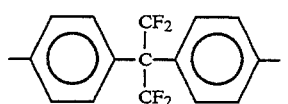

and $R_2$ is

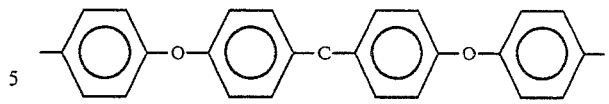

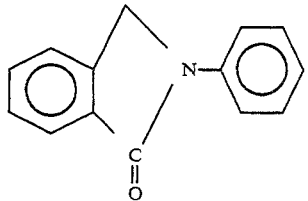

9. A poly(amide-ether-imide) as claimed in claim 1, wherein $R_1$ is

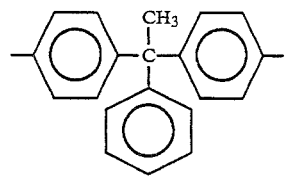

and $R_2$ is

10. A poly(amide-ether-imide) as claimed in claim 1, wherein $R^1$ is

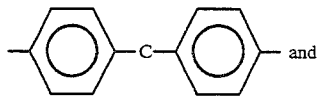 and

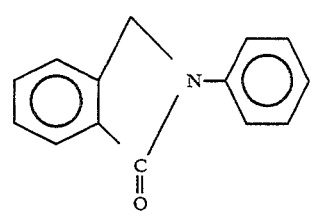

and $R_2$ is

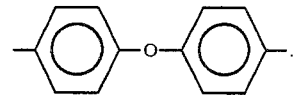

11. A poly(amide-ether-imide) as claimed in claim 1, wherein $R_1$ is

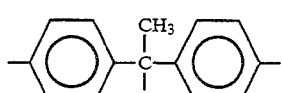

and $R_2$ is

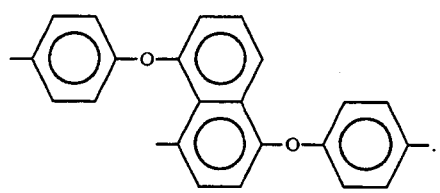

12. A poly(amide-ether-imide) as claimed in claim 1, wherein $R_1$ is

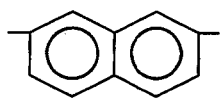

and $R_2$ is

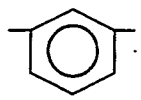

13. A poly(amide-ether-imide) as claimed in claim 1, wherein $R_1$ is

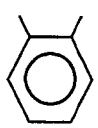

and $R_2$ is

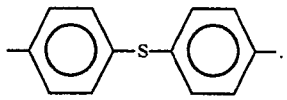

14. A poly (amide-ether-imide) as claimed in claim 1, wherein $R_1$ is

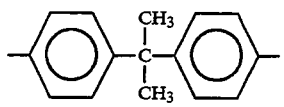

and $R_2$ is

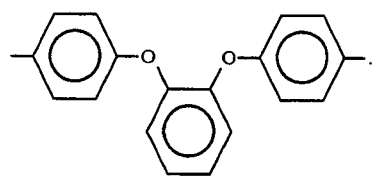

15. A poly(amide-ether-imide) as claimed in claim 1, wherein $R_1$ is

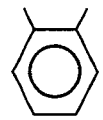

and $R^2$ is

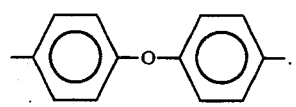

16. A method of preparing the poly(amide-ether-imide) (I) as described in claim 1, wherein said method comprising the steps of:

a) conducting a thermal condensation reaction by reacting an ether chain-containing aromatic diamine represented by formula III with trimellitic anhydride to form a diimide dicarboxylic acid represented by formula II in a polar solvent, wherein $R_1$ is defined as in claim 1; formula II is represented by the following formula:

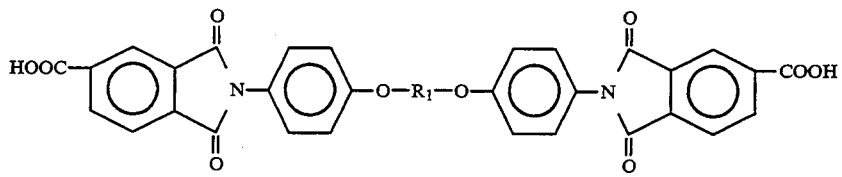

and formula III is represented by the following formula:

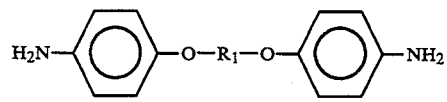

b) conducting a polycondensing reaction by reacting said diimide dicarboxytic acid represented by formula II and an aromatic diamine of the formula $H_2N-R_2-NH_2$ to form said poly(amide-ether-imide), wherein $R_2$ is defined as in claim 1.

* * * * *